(12) United States Patent
Hochschuler et al.

(10) Patent No.: US 6,740,093 B2
(45) Date of Patent: May 25, 2004

(54) METHOD AND APPARATUS FOR TREATING A VERTEBRAL BODY

(76) Inventors: Stephen Hochschuler, 17214 Club Hill Dr., Dallas, TX (US) 75248; Wesley Johnson, 8091 Spruce Trail, Eden Prairie, MN (US) 55347; Kevin L. Nickels, 8732 Walton Pond Cir., Bloomington, MN (US) 55438; Thomas R. Hektner, 825 Navajo Rd., Medina, MN (US) 55340; Larry Wales, 1654 Currie St., Maplewood, MN (US) 55119; Tyler Lipschultz, 15 S. First St., #A119, Minneapolis, MN (US) 55401

( * ) Notice: Subject to any disclaimer, the term of this patent is extended or adjusted under 35 U.S.C. 154(b) by 0 days.

(21) Appl. No.: 09/794,873

(22) Filed: Feb. 27, 2001

(65) Prior Publication Data

US 2002/0058947 A1 May 16, 2002

Related U.S. Application Data

(60) Provisional application No. 60/185,323, filed on Feb. 28, 2000, provisional application No. 60/220,303, filed on Jul. 24, 2000, provisional application No. 60/239,216, filed on Oct. 10, 2000, and provisional application No. 60/239,217, filed on Oct. 10, 2000.

(51) Int. Cl.$^7$ ................................. A61B 17/56
(52) U.S. Cl. ....................... 606/94; 623/11.11
(58) Field of Search .............. 606/92–94, 99; 623/16.11, 17.11, 17.12, 11.11, 17.15, 17.16

(56) References Cited

U.S. PATENT DOCUMENTS

| | | | | |
|---|---|---|---|---|
| 3,030,951 A | * | 4/1962 | Mandarino | 156/98 |
| 5,108,404 A | * | 4/1992 | Scholten et al. | 606/60 |
| 5,549,679 A | * | 8/1996 | Kuslich | 606/91 |
| 6,066,154 A | * | 5/2000 | Reiley et al. | 606/192 |
| 6,248,131 B1 | * | 6/2001 | Felt et al. | 606/61 |
| 6,383,190 B1 | * | 5/2002 | Preissman | 606/92 |

* cited by examiner

Primary Examiner—Eduardo C. Robert
Assistant Examiner—Michael B. Priddy
(74) Attorney, Agent, or Firm—Maginot, Moore & Beck (57) ABSTRACT

An implantable container is used to stabilize or restore height in a vertebral body. After insertion the container is filled with a bone filler material such as bone cement.

5 Claims, 12 Drawing Sheets

METHOD AND APPARATUS FOR TREATING A VERTEBRAL BODY

CROSS-REFERENCE TO RELATED CASES

The present case claims the benefit of the following Provisional Applications: "Cavity Sealing Barrier", Ser. No. 60/185,323, filed Feb. 28, 2000; "Implant for Hard Bones", Ser. No. 60/220,303, filed Jul. 24, 2000; "Vertebral Body Sealing Device and Method", Ser. No. 60/239,216, filed Oct. 10, 2000; "Hydraulic Distraction with Permeable Membrane", Ser. No. 60/239,217, filed Oct. 10, 2000 and incorporates each of these by reference in their entirety.

FIELD OF THE INVENTION

The present invention relates generally to the treatment of bones and more particularly to the treatment of the vertebral bodies found in the human spine.

BACKGROUND OF THE INVENTION

The human spine consists of a complex set of interrelated anatomic elements including a set of bones called vertebral bodies. Intervertebral discs separate most vertebral bodies. These discs includes a "spongy" nucleus pulpous surrounded by an annulus fibrosis "membrane". The annulus fibrosis connects the opposed endplates of adjacent vertebral bodies. All of these structures together with muscles act to provide motion, stability and protection for the spine. When healthy, these structures effectively protect the spinal cord and allow for normal motion.

However there are many disease states and aging processes that impact the patient. Osteoporosis and metastatic disease reduce the structural integrity of the vertebral bodies, predisposing them to fracture. Vertebral fractures can lead to loss of vertebral height which can exacerbate existing neurological condition or it can predispose the spine to other symptoms. Back pain often results from these conditions. Vertebroplasty is an effort to stabilize these fractures and to alleviate this source of pain.

Generally, fractures and loss of height if not treated results in a cascade of injury which is undesirable. For this reason various efforts have been directed at stabilizing and restoring the natural vertebral bodies of the back. Efforts have also been directed to replacing the vertebral bodies. condition or it can predispose the spine to other symptoms. Back pain often results from these conditions. Vertebroplasty is an effort to stabilize these fractures and to alleviate this source of pain.

Generally, fractures and loss of height if not treated results in a cascade of injury which is undesirable. For this reason various efforts have been directed at stabilizing and restoring the natural vertebral bodies of the back. Efforts have also been directed to replacing the vertebral bodies.

U.S. Pat. No. 5,108,404 to Scholten et al among others teaches a technique for height restoration that uses a bone cement product introduced into a cavity after a cavity has been made with an inflatable device. One problem with this system is the extravasation of bone cement to sensitive areas. Another problem is the difficulty of obtaining consistent control of height restoration with the Scholten system.

SUMMARY

In contrast to the prior art, the present invention involves both a container device that is permanently implanted and a method of using the container to stabilize the vertebral body or to restore height to the vertebral body.

In one embodiment the container is porous to the bone filler material. In another embodiment the container is impermeable to the bone filler material. In each embodiment the container controls and regulates the delivery of bone filler material into the vertebral body.

In one embodiment the container is flexible and conformal to the cavity. In another embodiment the container has a fixed shape which conforms to the cavity shape when deployed.

In one embodiment of the method, the bone filler is injected until the cavity is completely filled stabilizing the vertebral body. In another embodiment of the method the bone filler is injected and displaces the endplates of the vertebral body "restoring height" through a hydraulic jacking effect and stabilizing their vertebral body.

There are numerous bone filler materials which can be used to fill the container including bone cement and other materials. However it is a general property of the bone fillers that they must be injectable in a fluid state and that they harden.

BRIEF DESCRIPTION OF THE DRAWINGS

Throughout the several views of the drawings there are shown illustrative embodiments of the inventions in which like reference numerals indicate equivalent or identical structure, wherein.

DETAILED DESCRIPTION

The various container devices and the methods for using the container devices are disclosed in the context of the treatment of vertebral bodies. It should be recognized that the inventions may be used in other bones which present the same or similar pathologies, including but not limited to tibial plateaus, distal radius fractures, calcaneous fractures.

Figure 1:
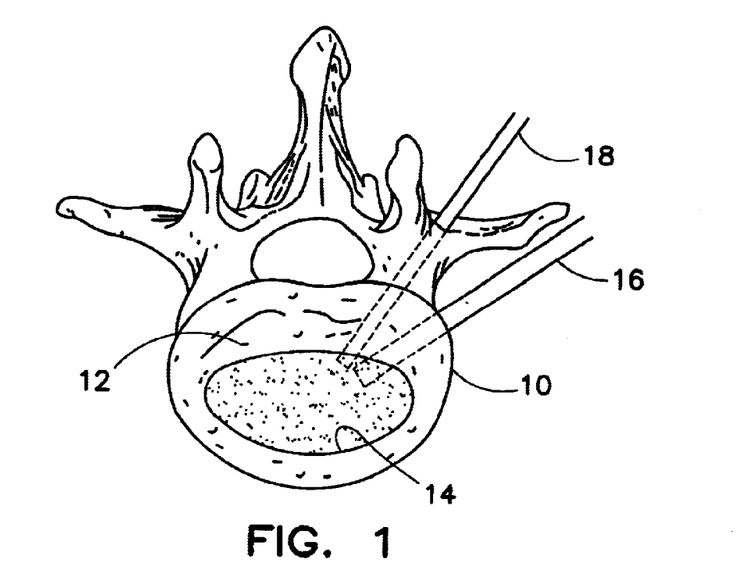
FIG. 1 is a sectional view of a vertebral body.
Figure 2:
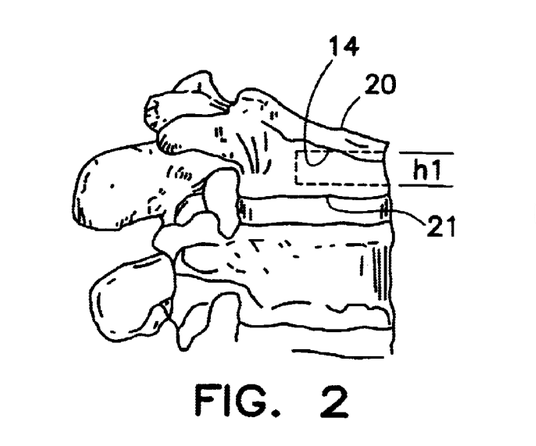
FIG. 2 is a view of a vertebral body in elevation.
Figure 3:
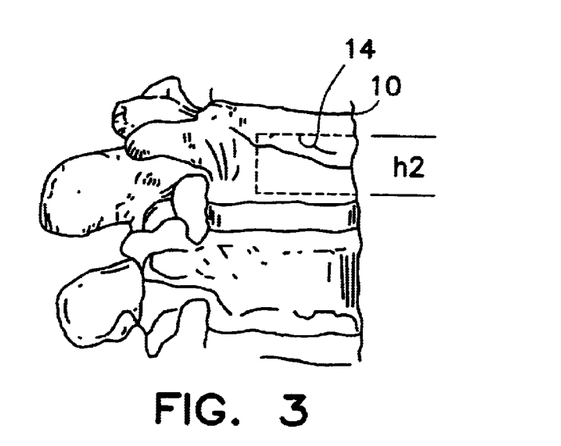
FIG. 3 is a view of a vertebral body in elevation.

FIG. 1, FIG. 2 and FIG. 3 taken together are intended to show a cavity creation process that precedes treatment with the devices and methods of the invention. In general cavity creation techniques are well known and they may include the creation of a cavity with a balloon device as is known in the art.

FIG. 1 shows a vertebral body 10 in partial cross section. The exterior portion of the vertebra is dense cortical bone and the interior is porous cancellous bone which is labeled 12 in the figure. The cavity 14 is depicted by the dashed outline in the drawing and it is formed in the porous bone. The shape of the cavity depends on the technique used to form it. This cavity is made in a conventional way. For example a tool may be introduced through extra-pedicular access tube 16 or transpedicular access tube 18 and operated in the vertebral body. As seen in the drawing the extra-pedicular access tube 16 may have a larger diameter and will be preferred by some surgeons. In general, the access approach for cavity creation will also be used for the introduction of the devices of the invention. These approaches will be used for the methods of the invention.

FIG. 2 shows a collapsed vertebral body 10 in elevation with a compression fracture and associated loss of height. The superior endplate 20 has moved due to a fracture and normal loading. The nominal height of the cavity formed in this vertebral body is labeled "h1" in the figure. As the end plate moves the angle formed between the superior endplate 20 and the inferior endplate 21 becomes acute which is undesirable. In the extreme case both sides of the endplates fall to form a severely compressed rectangular shaped vertebral body.

FIG. 3 shows a fractured vertebral body that requires intervention. In this vertebral body the height of the cavity 14 is indicated by the nominal height of the vertebral body labeled as "h2" in the figure.

Taken together the FIGS. 1, 2 and 3 represent the formation of a cavity 14 prior to treatment with device of the present invention.

Figure 4:
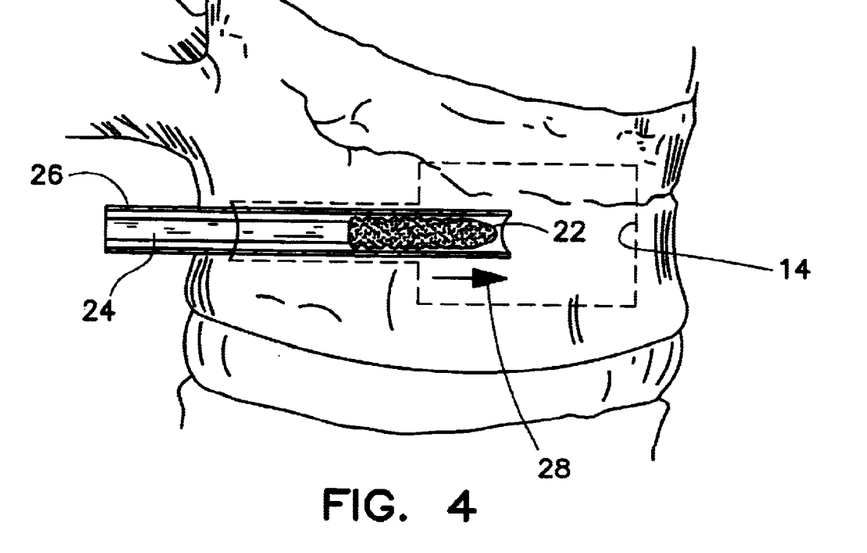
FIG. 4 is a view of a vertebral body with items shown in phantom view.
Figure 5:
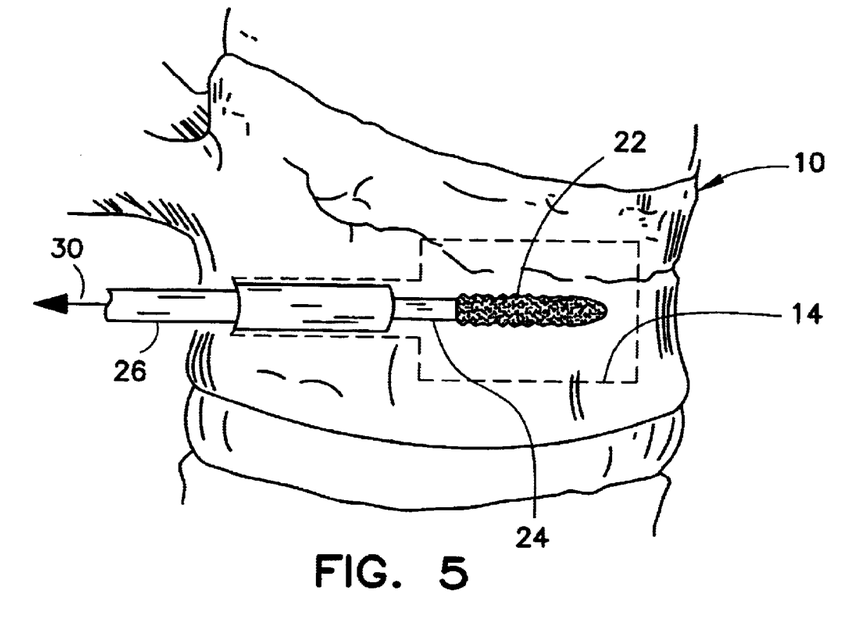
FIG. 5 is a view of a vertebral body with items shown in phantom view
Figure 6:
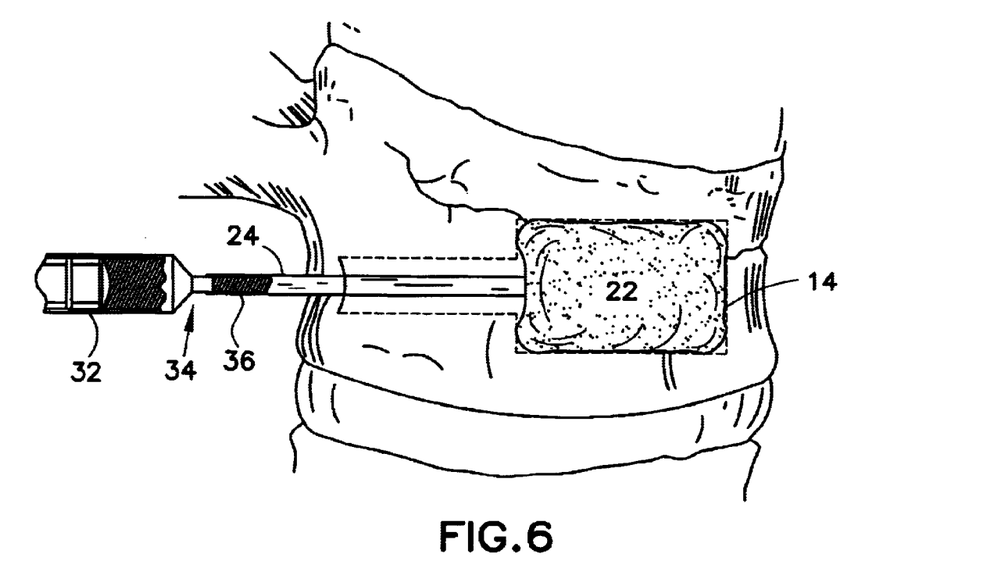
FIG. 6 is a view of a vertebral body with items shown in phantom view

Taken together FIG. 4 FIG. 5 and FIG. 6 represent steps in a method to stabilize a fractured vertebral body.

FIG. 4 shows a step in the method. In this drawing the container 22 is coupled to a fill tube 24 shown in phantom view. In this embodiment the container 22 is located at the distal end of a fill tube 24. The container 22 and fill tube 24 are carried together with the delivery tube 26. The motion arrow 28 indicates that the delivery tube 26 and fill tube 24 are being moved together into the surgically prepared cavity 14. The delivery tube 26 may be the same device that is used to deliver the cavity tools as discussed with reference to FIG. 1. Or the tube 26 may be a separate device inserted through an alternate access aperture.

FIG. 5 shows the deployment process step where the delivery tube 26 is retracted as indicated by motion arrow 30 while the fill tube 24 and the attached container 22 remain stationary in the vertebral body 10 cavity 14.

FIG. 6 shows the expansion of the container 22 within the cavity 14. The bone filler material 36 seen in phantom view has been loaded into the manually operated syringe 32 and the physician is injecting the material through the fill tube 24 into the container 22. The container 22 has unfurled and conformed to the shape of the cavity 14. The unconstrained shape of this container is generally cylindrical with spherical ends. This figure shows the deployment of the container in to a cavity which is substantially the same volume as the cavity 14. In this illustrative example the volume of the container is larger than the volume of the cavity and there is no stretching force applied to the impermeable container membrane.

The coupling 34 between the fill tube and the syringe 32 may be a conventional luer lock or other attachment device. Although a syringe is an effective filler delivery tool it is expected that physicians will use an alternative delivery system such as a an extruder rod inserted directly into the fill tube to displace bone filler into the container.

Figure 7:
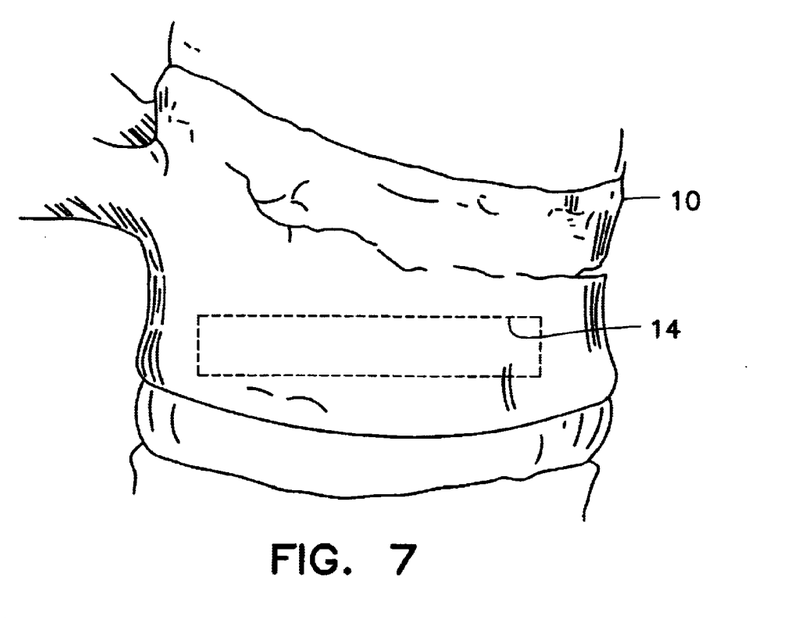
FIG. 7 is a view of a vertebral body with items shown in phantom view

FIG. 7 depicts the preliminary preparation of a cavity 14 in a collapsed vertebral body 10.

Figure 8:
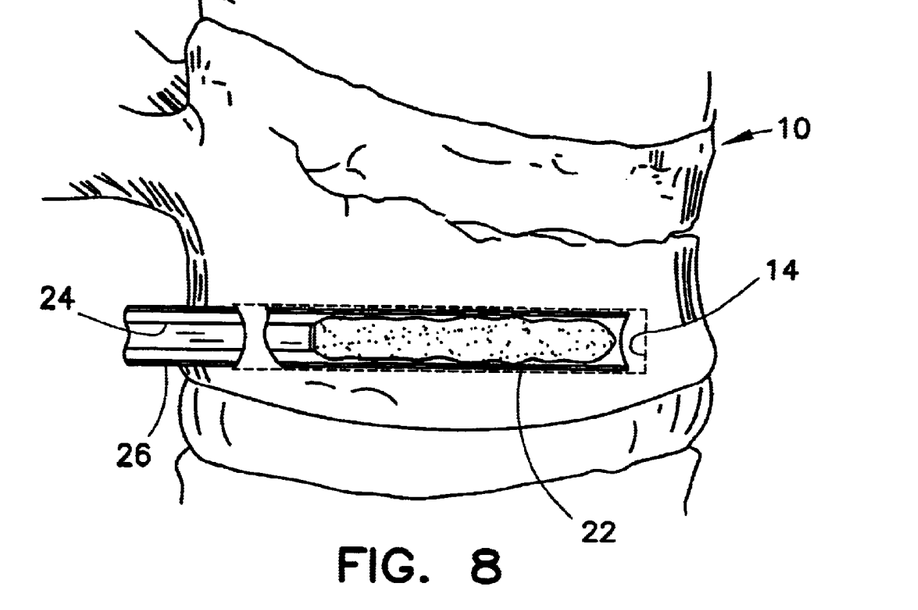
FIG. 8 is a view of a vertebral body with items shown in phantom view

FIG. 8 shows an introduction step in the hydraulic jacking process. In this illustration the container 22 and its attached fill tube 24 are inserted into the vertebral body 10 together with the delivery tube 26. The assembly is positioned in the cavity 14 proximate the end of the cavity. In this step care must be taken to prevent pressurizing the device within the pedicle.

Figure 9:
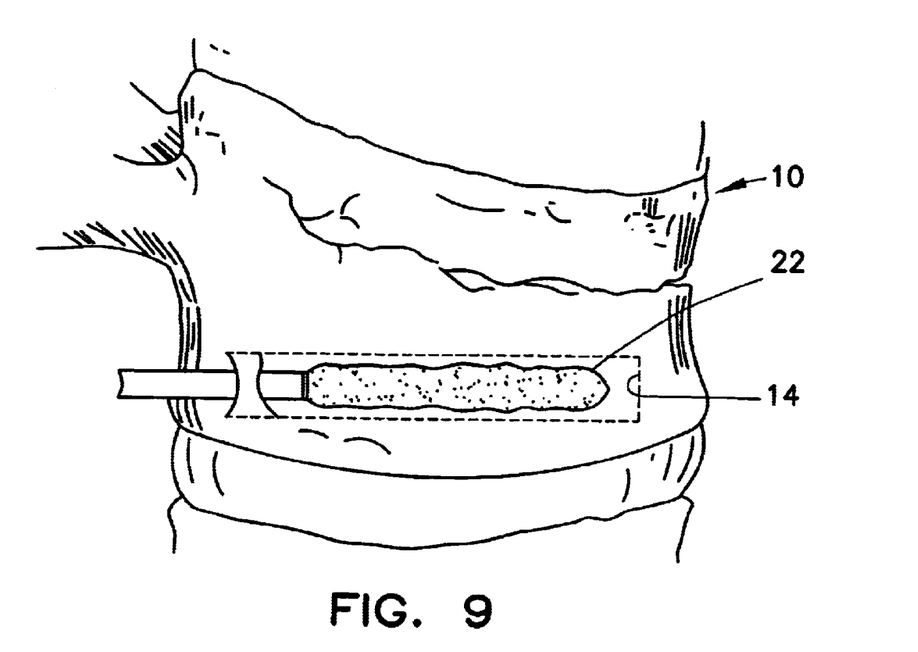
FIG. 9 is a view of a vertebral body with items shown in phantom view

FIG. 9 shows a deployment step in the process. In this illustration the container is fully deployed in the cavity 14 by withdrawing the delivery tube (not shown) from the fill tube leaving the container 22 exposed in the cavity 14.

Figure 10:
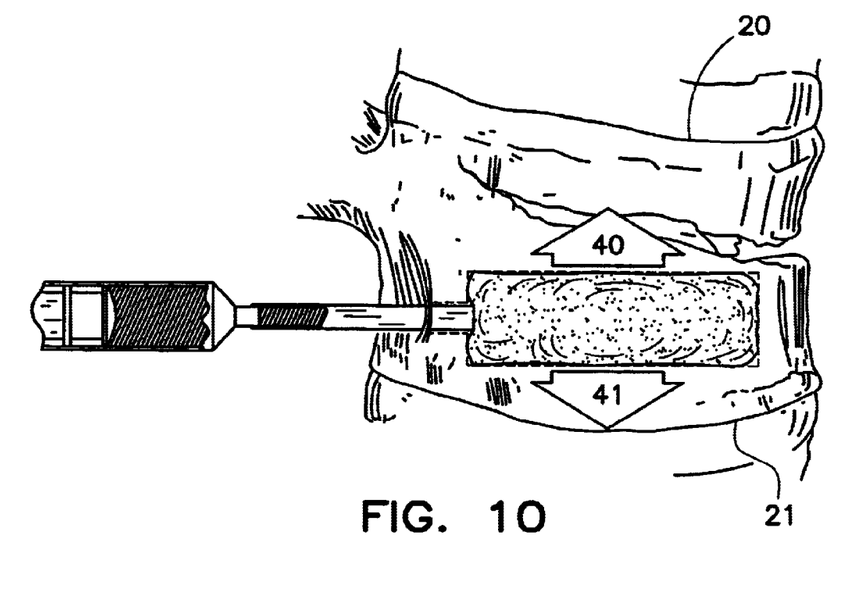
FIG. 10 is a view of a vertebral body with items shown in phantom view.

FIG. 10 shows an injection step in the process. The container 22 is filled through the fill tube 24 with a bone filler materials 36. The manual syringe 32 or other injection device injects the material at a sufficient pressure to create distraction forces shown in the figure a superior force 40 and inferior force 42. These forces are sufficient to move the endplate 20 and end plate 21 apart restoring height and angulation.

Figure 11:
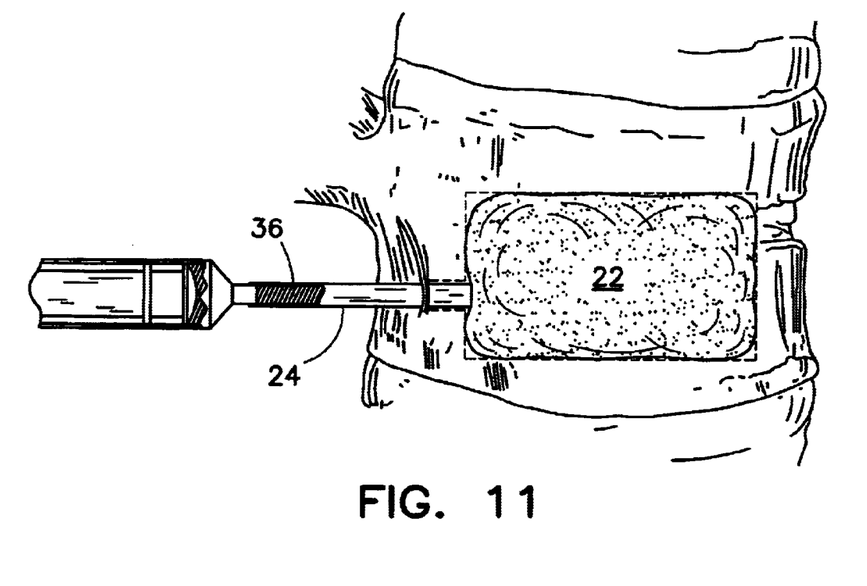
FIG. 11 is a view of a vertebral body with items shown in phantom view.

FIG. 11 shows a step of the process where an end point of the method is reached. Here the container 22 is completely filled and the original height of the vertebral body is restored. This end point can be determined in any of several ways. For example an inelastic fixed volume container can be used and the injecting process stopped when resistance is felt through the hydraulic connection with the container. An alternate approach is the injection of a fixed volume of bone filler into an oversized elastic or porous container 22. Also the physician may follow the injection under fluoroscopy and limit injection through observation of a real time image in combination with medical judgement. In this instance the container can be inelastic or elastic. The final step in the typical method will be to remove the fill tube 24 from the container 22. This step will typically be performed after the bone filler 36 material is "step up" and no longer in a low viscosity state.

These initial figures depict the stabilization method and the hydraulic jacking method performed with substantially cylindrical containers. The membranes in the examples have all been impermeable to the bone filler. In these process the container may be elastic or inelastic as may be desired by the physician.

The stabilization method may be performed with all of the container devices shown.

Figure 13:
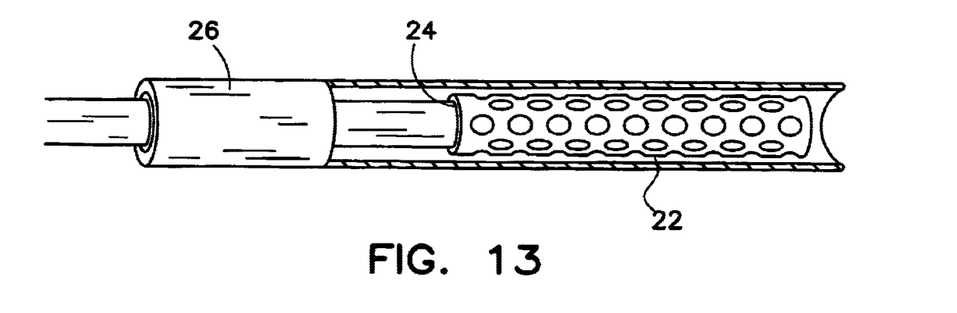
FIG. 13 is a view of an embodiment of a porous container.
Figure 14:
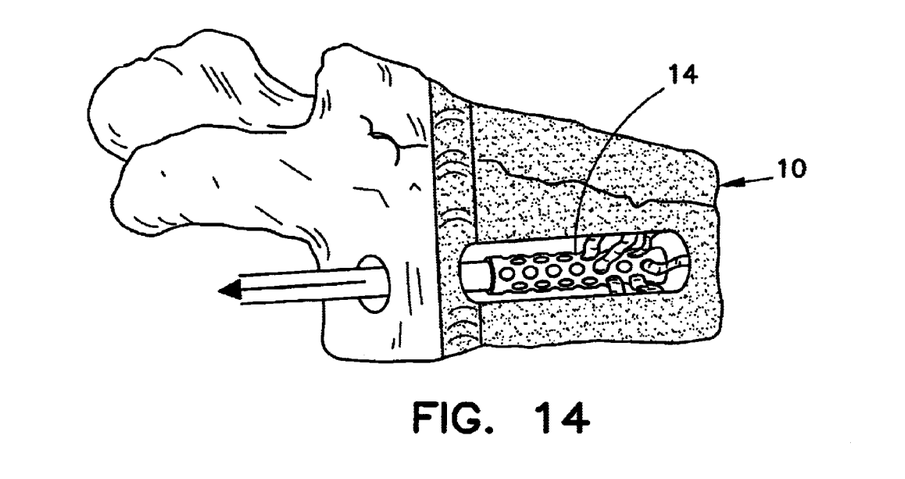
FIG. 14 is a view of a porous container in a cutaway vertebral body.

The hydraulic jacking method can be performed with the all of the container devices with the exception of FIG. 13 and FIG. 14.

Figure 12:
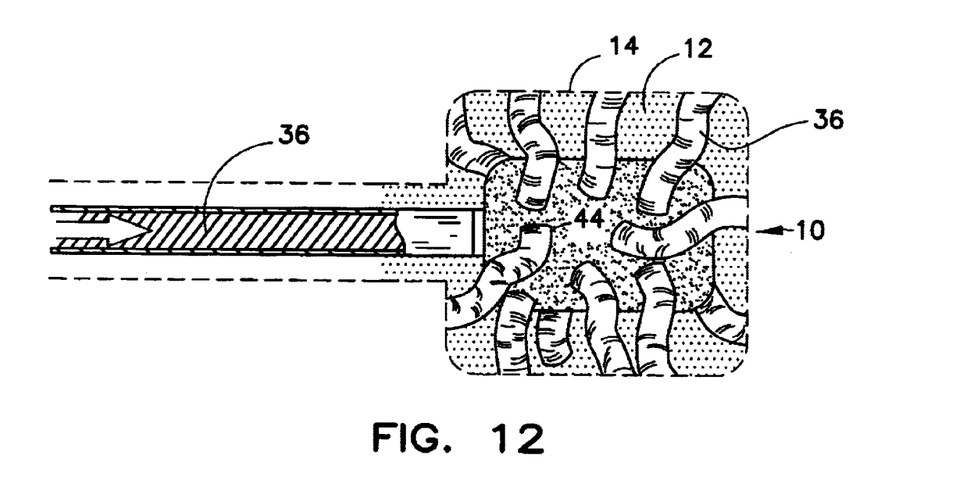
FIG. 12 is a view of an embodiment of a porous container in use.

FIG. 12 shows an alternate container 22 with a membrane perforated by a series of holes typified by hole 44. When placed in a vertebral body the bone filler 36 extrudes from the holes and interdigitates with the cancellous bone 12 inside the vertebral body 10. It is difficult to illustrate this process but the cavity 14 has a wall that is porous so the bone filler interdigitates with the cancellous bone matrix.

FIG. 13 shows a tubular fixed diameter form of the container 22 which can be used to control the delivery of bone filler to the cavity. The container 22 approximates the size and shape of the cavity, prior to bone filler injection. The holes in the device distribute the bone filler to locations next to the holes.

FIG. 14 shows the container of FIG. 13 in operation in a vertebral body 10.

One preferred method of use which can be performed with porous containers involves the injection of a first volume of relatively less viscous bone filler to promote interdigitation of the cancellous bone. Next a second injection of bone filler material with a different mechanical strength or chemical composition is injected and it "pushes" against the initial or primary injected material. This technique produces a gradient of strength and elasticity through the repaired bone which mimics the mechanical characteristics of the natural bone. The relatively small diameter of this device allow the set of apertures to distribute the various bone filler materials without moving the device during injection.

Another preferred method involves the same two stage injection process with a non-porous or impermeable container. In this instance there is negligible interdigitation but the gradient remains.

Figure 15:
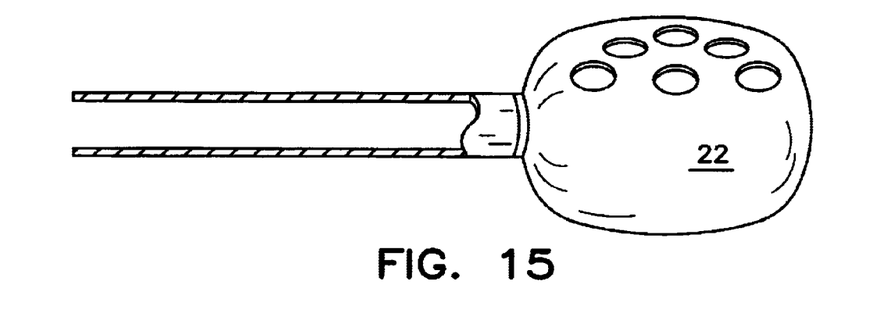
FIG. 15 is a view of a container in isolation.

FIG. 15 is a container with an asymmetrical distribution of holes so that the extrusion of bone filler occurs on one side of the container. This construction may allow the container to be moved within the vertebral body during injection of bone filler.

Figure 16:
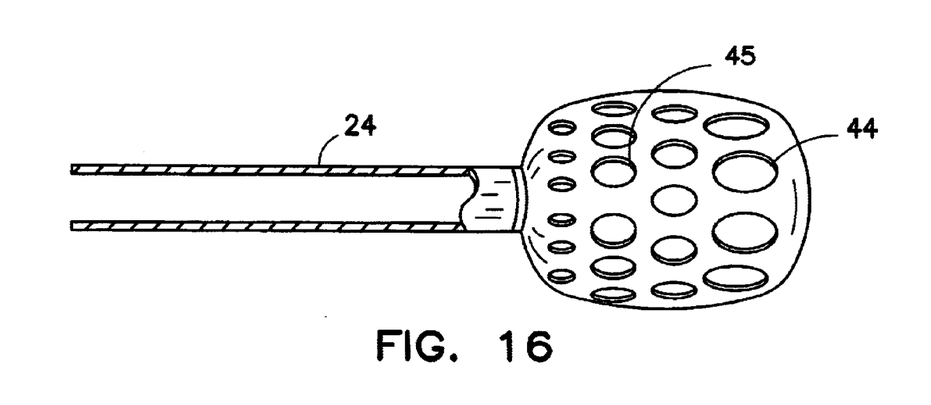
FIG. 16 is a view of a container in isolation.

FIG. 16 shows an asymmetrical container 22 where hole size and distribution vary over the surface of the membrane. For example hole 44 is larger than holes 45 which lie along the axis of the fill tube 24. This asymmetry provides physician control of the distribution and the flow of the bone filler materials into specific regions of the vertebral body.

Figure 17:
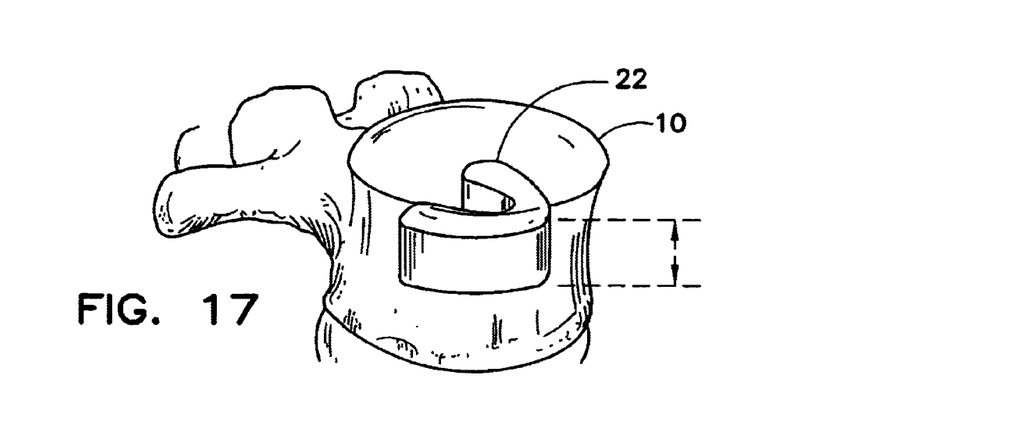
FIG. 17 is a perspective view of a container in a vertebral body.
Figure 18:
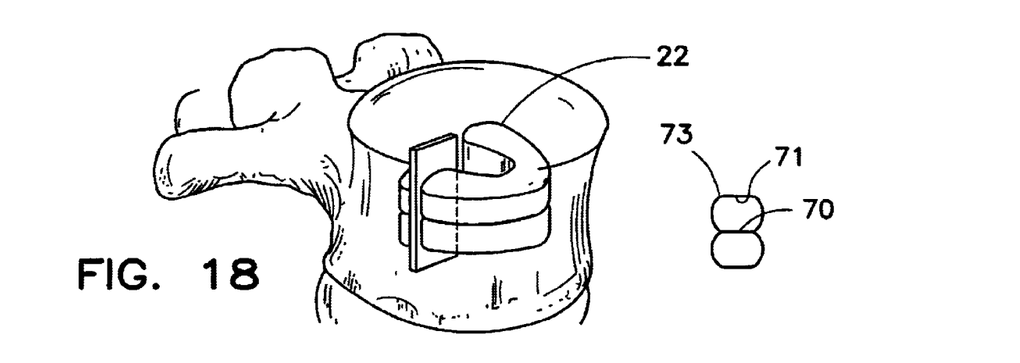
FIG. 18 is a perspective view of a container in a vertebral body.
Figure 19:
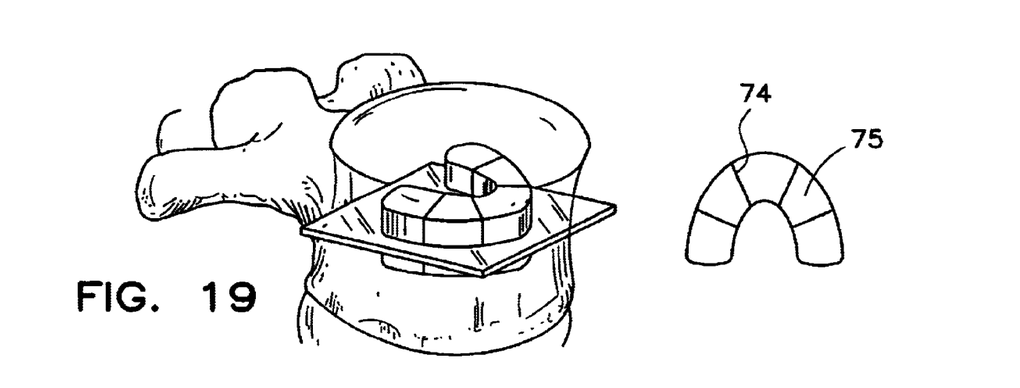
FIG. 19 is a perspective view of a container in a vertebral body.

FIG. 17, FIG. 18 and FIG. 19 should be considered together. This group of drawings depicts an alternate "horseshoe" shape for the construction for the container 22. In each instance the fill tube has been eliminated from the figure to improve clarity. However it should be understood that at least one fill tube is used with each container in these figures. All of the container devices depicted in FIG. 17 through FIG. 20 can be made of porous or non-porous membrane materials.

FIG. 17 is single chamber fixed volume device 22 which may expand to a nominal height in the vertebral body 10.

FIG. 18 is a segmented horseshoe shaped container 22 device with a horizontal rib 70 that divides the container into two separate structures. The inner of the membrane 71 may be continuous with this rib 70 or weep holes may be provided to facilitate flow of bone filler within the device. The exterior surface of the membrane 73 may be porous or impermeable to bone filler. In this embodiment the rib 70 will effectively limit the height achieved in the vertebral body.

FIG. 19 is multi-chambered device with several lateral compartments created by ribs typified by rib 74. In this embodiment the chambers typified by chamber 75 limit the horizontal extent of the growth of the container during the hydraulic jacking process.

Figure 20:
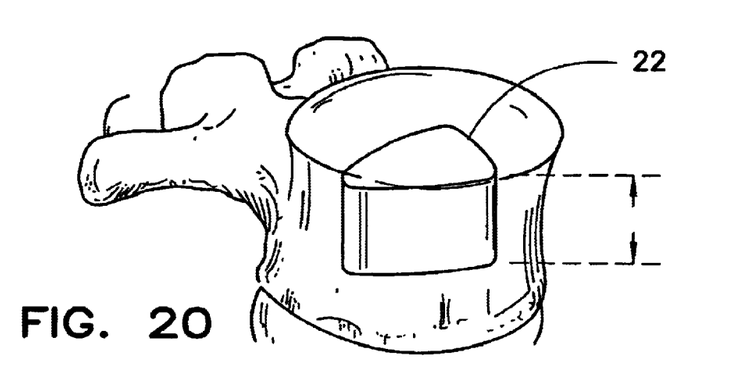
FIG. 20 is a perspective view of a container in a vertebral body.

FIG. 20 is single chamber fixed volume device 22 with a triangular "footprint".

Figure 21:
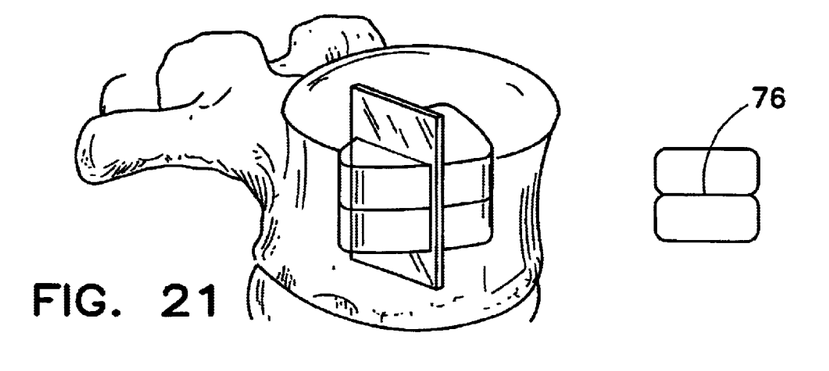
FIG. 21 is a perspective view of a container in a vertebral body

FIG. 21 is a segmented triangular device with a horizontal rib 76 defining two chambers.

Figure 22:
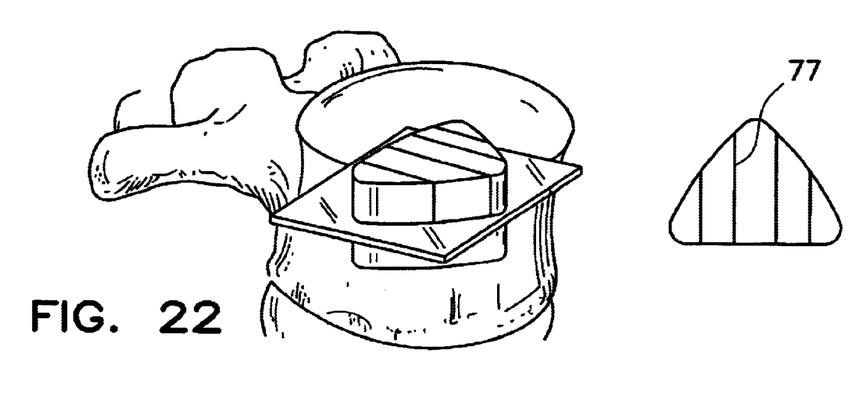
FIG. 22 is a perspective view of a container in a vertebral body

FIG. 22 is multi-chambered device with several lateral compartments created by ribs typified by rib 77.

Figure 23:
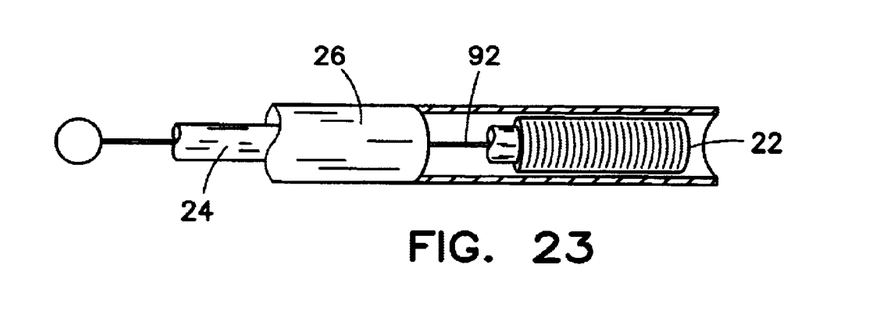
FIG. 23 is a view of a tubular container.

FIG. 23 shows an alternate tubular embodiment of a single chamber container 22 with a stylet 92 coupled to the most distal end of the container 22. This elongate tubular container is deployed by advancing the stylet 92 wire out of the delivery tube, which drags the container membrane out of the delivery tube 26 or the fill tube 24. In this device the container may be folded and placed entirely everted in the fill tube. This construction will allow the device to be safely delivered without the use of a delivery tube thereby maximizing the inner diameter of the fill tube.

Figure 24:
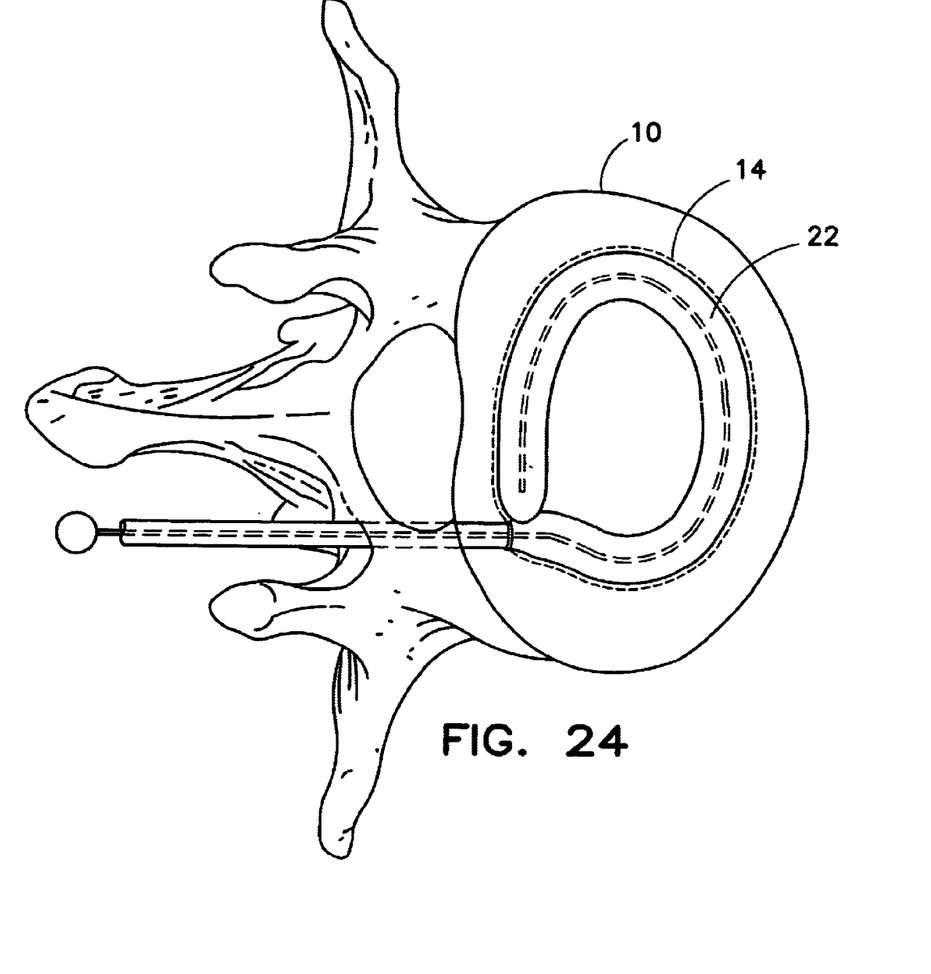
FIG. 24 is a view of a tubular container in use.

FIG. 24 shows the alternate tubular embodiment of the container in its partially filled configuration. In this illustration the vertebral body 10 has had an oval cavity 14 formed in the cancellous bone. The stylet 92 is used to force the container 22 along the outer wall path of the cavity 14 and it is then removed. Next bone filler material is injected through the fill tube and the annular ring tubular container is filled.

Figure 25:
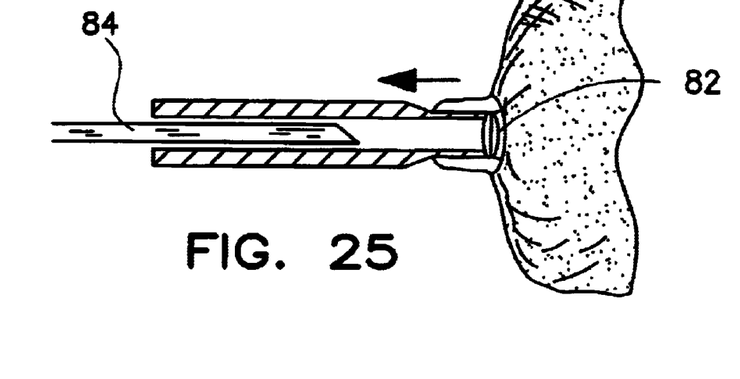
FIG. 25 is a view of a fill tube construction.

FIG. 25 shows a simple slip fit between the fill tube 24 and a complementary structure on the container 22. In this construction a septum 82 is used to fill the container 22 though a fill needle 84. One advantage of this construction is the septum seals the container and allows the container to seal while the bone filler hardens.

Figure 26:
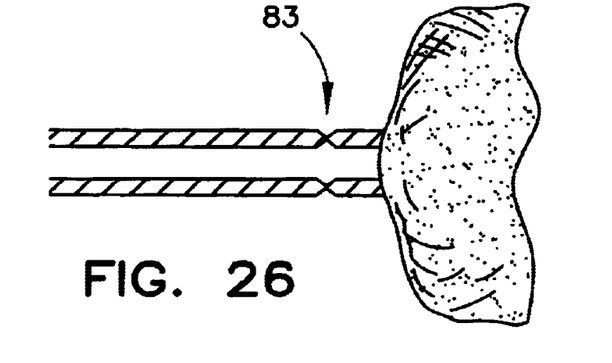
FIG. 26 is a view of a fill tube construction.

FIG. 26 shows are area or zone of weakness 83 in the fill tube 24 that preferentially breaks off to remove the fill tube from the container.

Figure 27:
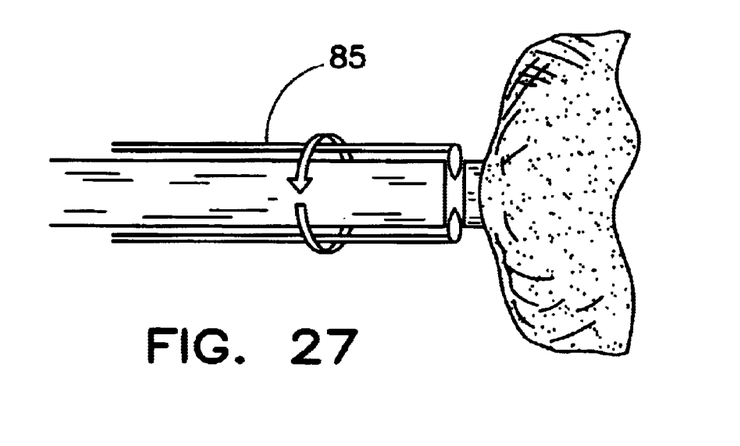
FIG. 27 is a view of a fill tube construction.

FIG. 27 the toothed member 85 circulates around the axis of the fill tube 24 and cuts of the fill tube away from the container after the bone filler has hardened.

Figure 28:
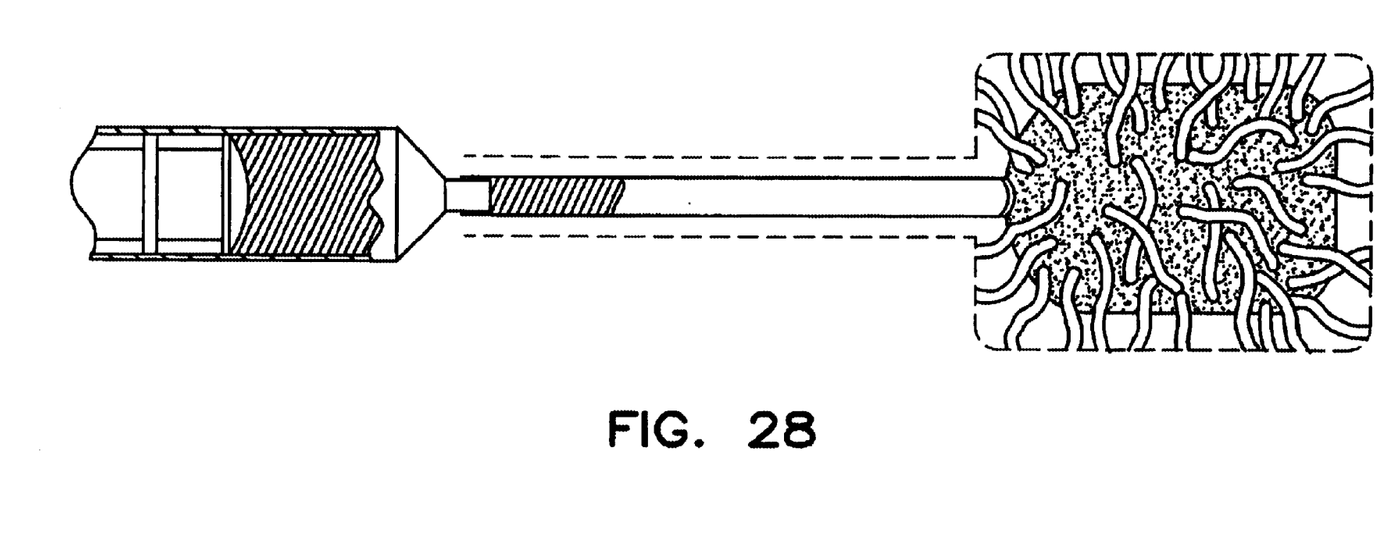
FIG. 28 is a view of an alternate porous container embodiment.

FIG. 28 shows the container formed as a porous woven membrane 90. In use the bone filler 36 will exude from the area between the woven fibers to permeate the cancellous bone. The woven mesh will produce the same effect as an elastic membrane.

Various materials may be used to make the container including, polyethylene Teflon, Gore-Tex, polybutylene terephathlate, polyethylene terephathalate glycol, urethane and urethane coated materials. The material or the construction can give rise to elastic or inelastic structures both of which are operable in the methods of the invention. The woven embodiments of the porous container may also be made from metal meshes or screens including titanium, elgiloy MP35 nitinol, stainless steel, or other bio-compatible metals.

Various bone fillers contemplated within the scope of this invention. Bone fillers are defined for this disclosure as any substance used to stabilize the bone and includes but is not limited to bone cement, human bone graft (allograft autograft), synthetic derived bone substitutes such as calcium phosphate and hydroxylapatite. Bone fillers may be supplemented with other biologically active materials including but not limited to collagen osteoinductive agents including bone morphogenic proteins. Other known ceramic based materials can be used as well. Other known bioresorbable polymers may be used as well.

Illustrative embodiments of the invention have been shown but numerous modifications may be made without departing from the scope of the invention which is defined by the appended claims.

What is claimed is:

1. A method of treating an vertebral body comprising the steps of:
    creating a cavity in the vertebral body through an access aperture;
    inserting a container into said vertebral body;
    said container having a fill passage coupled to said container;
    deploying said container within said vertebral body;
    injecting a bone filler material into said container through said fill passage.

2. A method of treating a vertebral body having a superior endplate and an inferior endplate, comprising the steps of:
    inserting a container into a vertebral body;
    deploying said container within said vertebral body;
        injecting a bone filler material selected from the group of: bone cement; human bone graft allograft; human bone graft autograft; synthetic derived bone substitute; sulfate and/or calcium phosphate, hydroxyapatite; into said container under pressure;
            whereby said pressure supplies a distraction force to move said inferior and superior endplates apart;
    ending injection after said endplates have moved apart.

3. A method of treating a vertebral body having a superior endplate and an inferior endplate, comprising the steps of:
    inserting a container into the vertebral body;
    deploying said container within said vertebral body;
    injecting a bone filler material into said container under pressure;
        whereby said pressure supplies a distraction force to move said superior and inferior endplates apart;
    ending injection after said endplates have moved apart.

4. A method of treating an vertebral body comprising the steps of:
    inserting a container into an vertebral body;
    said container having a fill passage coupled to said container;
        said container having a porous outer membrane sufficiently porous to allow filler material under pressure to leave the container after filling the container;
    deploying said container within said vertebral body injecting a filler material into said container through said fill passage with bone filler material in a sufficient volume to allow the bone filler material to exit the container and interdigitates with cancellous bone within said vertebral body thereby reinforcing said bone and stabilizing fractures in said bone;
    said container membrane porosity sufficient to provide resistance to the flow of said bone filler material to generate force to move the endplates of said vertebral body.

5. The method of claim 4 wherein said injecting step is ended after the superior and inferior endplates move toward a normal anatomic position.

* * * * *